United States Patent
Tanaka et al.

(10) Patent No.: US 12,035,892 B2
(45) Date of Patent: Jul. 16, 2024

(54) ENDOSCOPE SYSTEM, PROCESSOR FOR ENDOSCOPE, METHOD OF CONTROLLING ENDOSCOPE SYSTEM, AND RECORDING MEDIUM

(71) Applicant: OLYMPUS CORPORATION, Tokyo (JP)

(72) Inventors: Satoshi Tanaka, Hachioji (JP); Yoichiro Sakanoue, Fuchu (JP); Noriko Kohira, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 764 days.

(21) Appl. No.: 16/950,372

(22) Filed: Nov. 17, 2020

(65) Prior Publication Data
US 2021/0059503 A1 Mar. 4, 2021

Related U.S. Application Data

(63) Continuation of application No. PCT/JP2019/005085, filed on Feb. 13, 2019.

(30) Foreign Application Priority Data

May 21, 2018 (JP) ................................. 2018-096955

(51) Int. Cl.
*A61B 1/05* (2006.01)
*A61B 1/00* (2006.01)
(Continued)

(52) U.S. Cl.
CPC ............ *A61B 1/05* (2013.01); *A61B 1/00006* (2013.01); *A61B 1/00009* (2013.01);
(Continued)

(58) Field of Classification Search
CPC . A61B 1/00006; A61B 1/00096; A61B 1/063; A61B 1/0638; A61B 1/06;
(Continued)

(56) References Cited

U.S. PATENT DOCUMENTS

| 2011/0121200 A1* | 5/2011 | Watanabe | G01J 3/2803 |
| | | | 250/458.1 |
| 2015/0092035 A1* | 4/2015 | Yamamoto | A61B 1/0655 |
| | | | 348/370 |
| 2017/0095297 A1* | 4/2017 | Richmond | A61B 90/30 |

FOREIGN PATENT DOCUMENTS

| EP | 3 184 027 A1 | 6/2017 |
| EP | 3 190 785 A1 | 7/2017 |

(Continued)

OTHER PUBLICATIONS

International Search Report dated Apr. 9, 2019 received in PCT/JP2019/005085.

*Primary Examiner* — Michael J Carey
*Assistant Examiner* — Pamela F Wu
(74) *Attorney, Agent, or Firm* — Scully, Scott, Murphy & Presser, P.C.

(57) ABSTRACT

An endoscope system includes: a light source including one or more semiconductor light sources; an image pickup apparatus configured to pick up an image of the object irradiated with the illumination light to obtain the image; and a processor. The processor is configured to detect brightness of the image, to change one of a current value and an application period of a current applied to the semiconductor light source when the brightness of the image belongs to a first brightness range, to change the brightness of the image by predetermined processing, to which the image is subjected, when the brightness of the image belongs to a second brightness range, and to change the other of the current value and the application period of the current (Continued)

applied to the semiconductor light source when the brightness of the image belongs to a third brightness range.

8 Claims, 7 Drawing Sheets

(51) Int. Cl.
  *A61B 1/06* (2006.01)
  *H04N 23/71* (2023.01)
  *H04N 23/74* (2023.01)
(52) U.S. Cl.
  CPC ........ *A61B 1/00045* (2013.01); *A61B 1/0655* (2022.02); *A61B 1/0684* (2013.01); *H04N 23/71* (2023.01); *H04N 23/74* (2023.01)

(58) Field of Classification Search
  CPC ...... A61B 1/0661–0692; A61B 1/0655; A61B 1/00163; A61B 1/00009; A61B 1/000094; A61B 1/000095; A61B 1/00165; A61B 1/04; A61B 1/043; A61B 1/045; A61B 1/05; A61B 1/0605–0627; A61B 1/00004; H04N 23/70–71
  USPC .................................................. 600/118, 160
  See application file for complete search history.

(56) References Cited

FOREIGN PATENT DOCUMENTS

| | | |
|---|---|---|
| JP | 11-253397 A | 9/1999 |
| JP | 2017-060860 A | 3/2017 |
| WO | 2016/035829 A1 | 3/2016 |
| WO | 2016/125334 A1 | 8/2016 |

\* cited by examiner

ENDOSCOPE SYSTEM, PROCESSOR FOR ENDOSCOPE, METHOD OF CONTROLLING ENDOSCOPE SYSTEM, AND RECORDING MEDIUM

CROSS REFERENCE TO RELATED APPLICATION

This application is a continuation application of PCT/JP2019/005085 filed on Feb. 13, 2019 and claims benefit of Japanese Application No. 2018-096955 filed in Japan on May 21, 2018, the entire contents of which are incorporated herein by this reference.

BACKGROUND OF THE INVENTION

1. Field of the Invention

The present invention relates to an endoscope system, and more particularly to an endoscope system used for observation of an object existing in a subject.

2. Description of the Related Art

In endoscope observation in a medical field, a semiconductor light source such as an LED may be used as a light source that generates illumination light for illuminating an object such as a living tissue in a subject.

More specifically, for example, in an endoscope apparatus disclosed in Japanese Patent Application Laid-Open Publication No. 11-253397 in which a white light emitting diode is provided at a distal end portion of an electronic endoscope, control is performed for setting a light emitting time of the white light emitting diode to a maximum light emitting time, and then control is performed for allowing the white light emitting diode to emit light with a drive current value larger than an initial drive current value.

SUMMARY OF THE INVENTION

An endoscope system includes: a light source configured to generate illumination light for illuminating an object existing in a subject, the light source including one or more semiconductor light sources; an image pickup apparatus configured to pick up an image of the object irradiated with the illumination light to obtain the image; and a processor. The processor is configured to: detect brightness of the image, and perform an operation according to a first control pattern in which first control is performed to change one of a current value and an application period of a current applied to the semiconductor light source, which is a generation source of the illumination light, when the brightness of the image belongs to a first brightness range, second control is performed to change the brightness of the image by predetermined processing, to which the image is subjected, when the brightness of the image belongs to a second brightness range brighter than the first brightness range, and third control is performed to change another of the current value and the application period of the current applied to the semiconductor light source, which is a generation source of the illumination light, when the brightness of the image belongs to a third brightness range brighter than the second brightness range.

A processor for endoscope, capable of being connected to a light source apparatus and an endoscope, the light source apparatus being configured to generate illumination light for illuminating an object existing in a subject, the light source apparatus including one or more semiconductor light sources, the endoscope being configured to pick up an image of the object irradiated with the illumination light to obtain the image, the processor for endoscope being configured to: detect brightness of the image; and perform an operation according to a first control pattern in which first control is performed to change one of a current value and an application period of a current applied to the semiconductor light source, which is a generation source of the illumination light, when the brightness of the image belongs to a first brightness range, second control is performed to change the brightness of the image by predetermined processing, to which the image is subjected, when the brightness of the image belongs to a second brightness range brighter than the first brightness range, and third control is performed to change another of the current value and the application period of the current applied to the semiconductor light source, which is a generation source of the illumination light, when the brightness of the image belongs to a third brightness range brighter than the second brightness range.

A method of controlling an endoscope system including a light source apparatus and an endoscope, the light source apparatus being configured to generate illumination light for illuminating an object existing in a subject, the light source apparatus including one or more semiconductor light sources, the endoscope being configured to pick up an image of the object irradiated with the illumination light to obtain the image, the method including: detecting brightness of the image; performing first control to change one of a current value and an application period of a current applied to the semiconductor light source, which is a generation source of the illumination light, when the brightness of the image belongs to a first brightness range; performing second control to change the brightness of the image by predetermined processing, to which the image is subjected, when the brightness of the image belongs to a second brightness range brighter than the first brightness range; and performing third control to change another of the current value and the application period of the current applied to the semiconductor light source, which is a generation source of the illumination light, when the brightness of the image belongs to a third brightness range brighter than the second brightness range.

A computer-readable recording medium being a non-transitory computer-readable recording medium that stores an image processing program which a computer is caused to execute, the computer-readable recording medium causing an endoscope system to execute a detection process and a control process, the endoscope system including a light source apparatus and an endoscope, the light source apparatus being configured to generate illumination light for illuminating an object existing in a subject, the light source apparatus including one or more semiconductor light sources, the endoscope being configured to pick up an image of the object irradiated with the illumination light to obtain the image, the detection process being a process of detecting brightness of the image, the control process being a process in which first control is performed to change one of a current value and an application period of a current applied to the semiconductor light source, which is a generation source of the illumination light, when the brightness of the image belongs to a first brightness range, second control is performed to change the brightness of the image by predetermined processing, to which the image is subjected, when the brightness of the image belongs to a second brightness range brighter than the first brightness range, and third control is performed to change another of the current value and the application period of the current applied to the semiconductor light source, which is a generation source of the illumination light, when the brightness of the image belongs to a third brightness range brighter than the second brightness range.

DETAILED DESCRIPTION OF THE PREFERRED EMBODIMENT

An embodiment of the present invention will be described below with reference to the drawings.

FIGS. 1 to 11 relate to the embodiment of the present invention.

Figure 1:
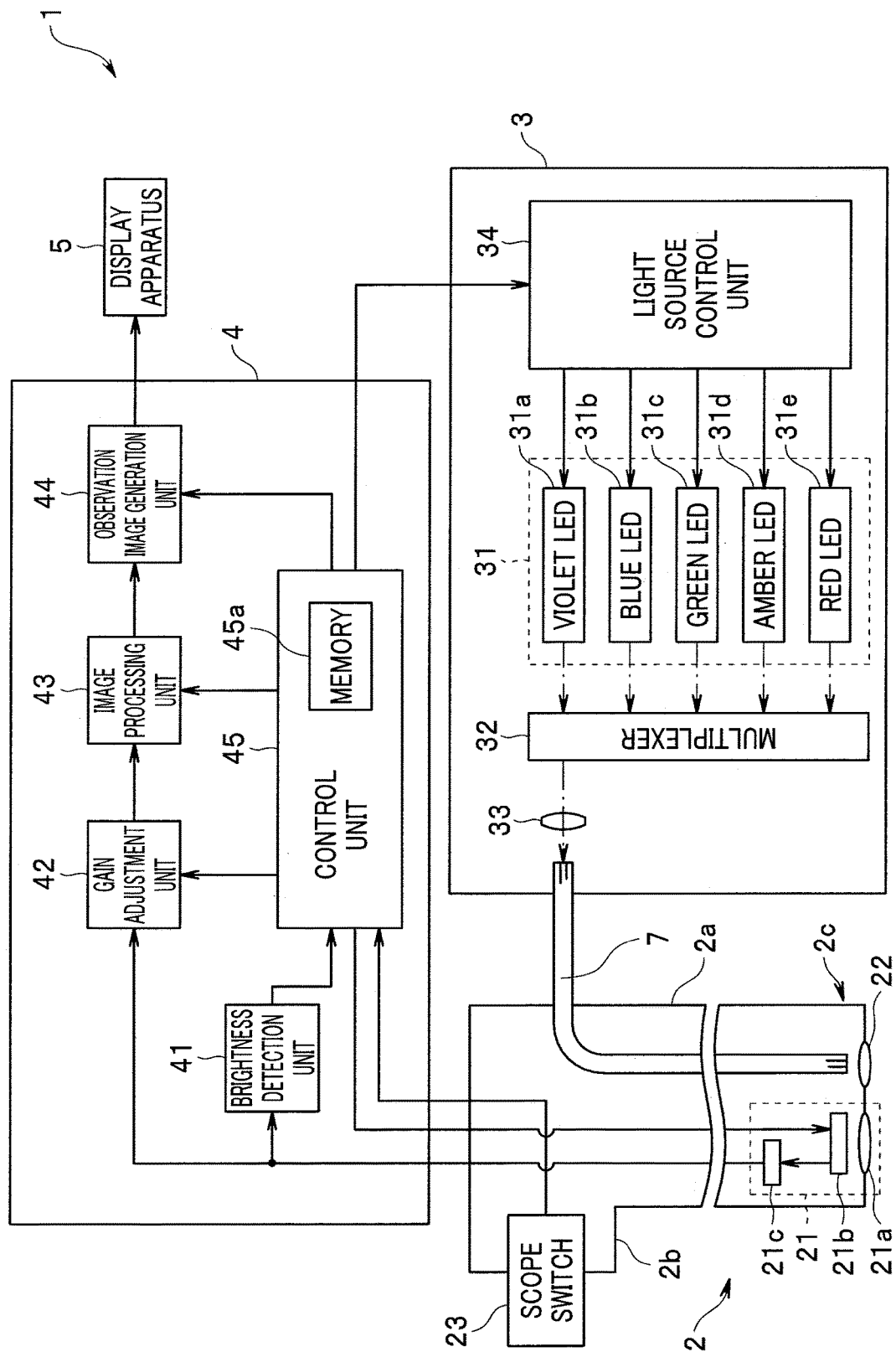
FIG. 1 is a diagram illustrating a configuration of main parts of an endoscope system according to an embodiment.

As shown in FIG. 1, an endoscope system 1 includes an endoscope 2 configured to be insertable into a subject and output image data obtained by an image pickup of an object such as a living tissue existing within the subject, a light source apparatus 3 configured to supply illumination light used to observe the object via a light guide 7 arranged to be inserted into the endoscope 2, a processor 4 configured to generate and output an observation image corresponding to the image data outputted from the endoscope 2, and a display apparatus 5 configured to display on a screen the observation image outputted from the processor 4. FIG. 1 is a diagram showing a configuration of main parts of the endoscope system according to the embodiment.

The endoscope 2 includes an insertion portion 2a formed in an elongated shape and insertable into the subject and an operation section 2b provided on a proximal end side of the insertion portion 2a. The endoscope 2 is configured to be detachably connected to the processor 4 via a universal cable (not shown) containing a signal line used for transmitting the image data outputted from an image pickup unit 21 (to be described below), for example. The endoscope 2 is configured to be detachably connected to the light source apparatus 3 via a light guide cable (not shown) containing at least a part of the light guide 7.

A distal end portion 2c of the insertion portion 2a is provided with an image pickup unit 21 configured to pick up an image of the object such as the living tissue within the subject, an emission end portion of the light guide 7, and an illumination optical system 22 configured to irradiate the object with the illumination light transmitted via the light guide 7.

The image pickup unit 21 is configured to pick up an image of the object illuminated with the illumination light passing through the illumination optical system 22 to generate image data, and to output the generated image data to the processor 4. In other words, the image pickup unit 21 is configured to pick up an image of the object illuminated with the illumination light passing through the illumination optical system 22 to obtain an image. Further, the image pickup unit 21 includes an objective optical system 21a, an image pickup device 21b, and an Analog Front End (hereinafter, abbreviated as AFE) 21c.

The objective optical system 21a includes, for example, an optical device such as a lens and is configured to form an image of return light (reflected light) emitted from the object irradiated with the illumination light passing through the illumination optical system 22.

The image pickup device 21b includes an image sensor such as a CCD or a CMOS. An image pickup surface of the image pickup device 21b is provided with a color filter having a primary color Bayer arrangement for dispersing the return light incident from the objective optical system 21a into three colors of red, green, and blue and a plurality of pixels arranged in a matrix shape for an image pickup of light passing through the color filter. The image pickup device 21b is configured to generate an image pickup signal by performing image pickup of the return light formed by the objective optical system 21a and output the generated image pickup signal to the AFE 21c. In addition, the image pickup device 21b is configured to perform an operation in response to a control signal outputted from the processor 4.

The AFE 21c is configured to perform predetermined signal processing such as noise reduction processing and A/D conversion processing on the image pickup signal outputted from the image pickup device 21b to generate image data, and to output the generated image data to the processor 4.

The operation section 2b has a shape that a user can grasp to operate. The operation section 2b is provided with a scope switch 23 including one or more switches capable of issuing an instruction in response to an input operation of the user to the processor 4. More specifically, the scope switch 23 includes an observation mode changeover switch (not shown) capable of issuing an instruction to set (switch) an observation mode of the endoscope system 1 to either of a white light observation mode and a special light observation mode in response to a user's operation, for example. In the present embodiment, an observation mode changeover switch similar to the scope switch 23 may be provided in the processor 4.

The light source apparatus 3 is configured to generate illumination light for illuminating the object existing in the subject. In addition, the light source apparatus 3 includes a light emitting unit 31, a multiplexer 32, a condenser lens 33, and a light source control unit 34.

The light emitting unit 31 includes a violet LED 31a, a blue LED 31b, a green LED 31c, an amber LED 31d, and a red LED 31e. In other words, the light emitting unit 31 includes a plurality of semiconductor light sources (semiconductor light emitting devices).

The violet LED 31a is configured to generate violet light (hereinafter, referred to as V light) having a peak wavelength (center wavelength) in a violet range. More specifically, the violet LED 31a is configured to generate light having a peak wavelength set around 415 nm as V light, for example. Further, the violet LED 31a is configured to emit or quench light in response to an LED drive signal supplied from the light source control unit 34. The violet LED 31a is configured to emit light with a light emission amount according to the LED drive signal supplied from the light source control unit 34. Note that a light emission amount EV of the violet LED 31a is defined as a total amount of light obtained by integration of intensities of light respectively having wavelengths included in a wavelength band of the V light.

The blue LED 31b is configured to generate blue light (hereinafter, referred to as B light) having a peak wavelength (center wavelength) in a blue range belonging to a longer wavelength than the V light. More specifically, the blue LED 31b is configured to generate light having a peak wavelength set around 460 nm as B light, for example. Further, the blue LED 31b is configured to emit or quench light in response to the LED drive signal supplied from the light source control unit 34. The blue LED 31b is configured to emit light with a light emission amount according to the LED drive signal supplied from the light source control unit 34. Note that a light emission amount EB of the blue LED 31b is defined as a total amount of light obtained by integration of intensities of light respectively having wavelengths included in a wavelength band of the B light.

The green LED 31c is configured to generate green light (hereinafter, referred to as G light) having a peak wavelength (center wavelength) in a green range belonging to a longer wavelength than the B light. More specifically, the green LED 31c is configured to generate light having a peak wavelength set around 540 nm as G light, for example. Further, the green LED 31c is configured to emit or quench light in response to the LED drive signal supplied from the light source control unit 34. The green LED 31c is configured to emit light with a light emission amount according to the LED drive signal supplied from the light source control unit 34. Note that a light emission amount EG of the green LED 31c is defined as a total amount of light obtained by integration of intensities of light respectively having wavelengths included in a wavelength band of the G light.

The amber LED 31d is configured to generate amber light (hereinafter, referred to as A light) having a peak wavelength (center wavelength) in an amber range belonging to a longer wavelength than the G light. More specifically, the amber LED 31d is configured to generate light having a peak wavelength set around 600 nm as A light, for example. Further, the amber LED 31d is configured to emit or quench light in response to the LED drive signal supplied from the light source control unit 34. The amber LED 31d is configured to emit light with a light emission amount according to the LED drive signal supplied from the light source control unit 34. Note that a light emission amount EA of the amber LED 31d is defined as a total amount of light obtained by integration of intensities of light respectively having wavelengths included in a wavelength band of the A light. In the present embodiment, the peak wavelength of the A light emitted from the amber LED 31d may be set to any wavelength between 585 nm and 615 nm.

The red LED 31e is configured to generate red light (hereinafter, referred to as R light) having a peak wavelength (center wavelength) in a red range belonging to a longer wavelength than the A light. More specifically, the red LED 31e is configured to generate light having a peak wavelength set around 630 nm as R light, for example. Further, the red LED 31e is configured to emit or quench light in response to the LED drive signal supplied from the light source control unit 34. The red LED 31e is configured to emit light with a light emission amount according to the LED drive signal supplied from the light source control unit 34. Note that a light emission amount ER of the red LED 31e is defined as a total amount of light obtained by integration of intensities of light respectively having wavelengths included in a wavelength band of the R light.

The multiplexer 32 is configured to be able to multiplex the respective lights emitted from the light emitting unit 31 and make the multiplexed lights incident on the condenser lens 33.

The condenser lens 33 is configured to condense the light incident through the multiplexer 32 and emit the condensed lights to an incident end portion of the light guide 7.

The light source control unit 34 includes a control circuit and a drive circuit, for example. The light source control unit 34 is configured to generate and output an LED drive signal, which is a pulse-shaped drive signal to drive respective LEDs of the light emitting unit 31, based on the control signal outputted from the processor 4.

The processor 4 includes a brightness detection unit 41, a gain adjustment unit 42, an image processing unit 43, an observation image generation unit 44, and a control unit 45.

The brightness detection unit 41 includes a brightness detection circuit, for example. In addition, the brightness detection unit 41 is configured to perform brightness detection processing, which is processing for detecting brightness of the image data outputted from the endoscope 2, to generate brightness detection information indicating the brightness detected by the brightness detection processing, and to output the information to the control unit 45.

The gain adjustment unit 42 includes a gain adjustment circuit, for example. In addition, the gain adjustment unit 42 is configured to set a gain value GV in response to the control signal outputted from the control unit 45 and to perform gain adjustment processing for multiplying the image data outputted from the endoscope 2 by the set gain value GV. The gain adjustment unit 42 is configured to output the image data subjected to the above-described gain adjustment processing to the image processing unit 43.

The image processing unit 43 includes an image processing circuit, for example. The image processing unit 43 is configured to perform color separation processing on the image data outputted from the gain adjustment unit 42, based on the control signal outputted from the control unit 45 and to output the image data obtained by the color separation processing to the observation image generation unit 44.

The observation image generation unit 44 includes an image generation circuit, for example. The observation image generation unit 44 is configured to, based on the control signal outputted from the control unit 45, generate an observation image using the image data outputted from the image processing unit 43 and to output the generated observation image to the display apparatus 5.

The control unit 45 includes a control circuit, for example. The control unit 45 is configured to generate and output a control signal for causing an operation to be performed in response to an instruction from the scope switch 23. Further, the control unit 45 is configured to generate and output a control signal for controlling the operation of the image pickup device 21b.

The control unit 45 includes a memory 45a that stores control information for white light observation (hereinafter, abbreviated as control information WCJ) indicating a control content to be performed by the control unit 45 in a white light observation mode and control information for special light observation (hereinafter, abbreviated as control information SCJ) indicating a control content to be performed by the control unit 45 in a special light observation mode.

The above-described control information WCJ includes, for example, brightness control information for white light observation (hereinafter, abbreviated as brightness control information WBCJ) which is information used at the time of controlling brightness of an observation image WLG displayed on the display apparatus 5 in the white light observation mode. In addition the above-described control information SCJ includes, for example, brightness control information for special light observation (hereinafter, abbreviated as brightness control information SBCJ) which is information used at the time of controlling brightness of an observation image SLG displayed on the display apparatus 5 in the special light observation mode.

When detecting that the instruction to set the observation mode of the endoscope system 1 to the white light observation mode has been issued, the control unit 45 is configured to read the control information WCJ from the memory 45a and to generate and output a control signal for causing an operation to be performed according to the read control information WCJ. Further, when detecting that the instruction to set the observation mode of the endoscope system 1 to the white light observation mode has been issued, the control unit 45 is configured to set a brightness target value TWA in the white light observation mode. Further, when detecting that the instruction to set the observation mode of the endoscope system 1 to the white light observation mode has been issued, the control unit 45 is configured to, based on the brightness detection information outputted from the brightness detection unit 41 and the brightness control information WBCJ included in the control information WCJ, perform an operation related to brightness control such that the brightness of the observation image WLG displayed on the display apparatus 5 is closer to the brightness target value TWA.

When detecting that the instruction to set the observation mode of the endoscope system 1 to the special light observation mode has been issued, the control unit 45 is configured to read the control information SCJ from the memory 45a and to generate and output a control signal for causing an operation to be performed according to the read control information SCJ. Further, when detecting that the instruction to set the observation mode of the endoscope system 1 to the special light observation mode has been issued, the control unit 45 is configured to set a brightness target value TSA in the special light observation mode. Further, when detecting that the instruction to set the observation mode of the endoscope system 1 to the special light observation mode has been issued, the control unit 45 is configured to, based on the brightness detection information outputted from the brightness detection unit 41 and brightness control information SBCJ included in the control information SCJ, perform an operation related to brightness control such that the brightness of the observation image SLG displayed on the display apparatus 5 is closer to the brightness target value TSA.

In other words, the control unit 45 is configured to, based on the instruction from the scope switch 23 and the control information read from the memory 45a, perform an operation for setting the observation mode of the endoscope system 1 to either a white light observation mode or a special light observation mode. In addition, the control unit 45 has a function as an illumination mode switching unit, and is configured to perform an operation for switching an illumination mode in which the object is irradiated with the illumination light emitted from the light source apparatus 3 to either an illumination mode in which the object is irradiated with illumination light WL to be described below or an illumination mode in which the object is irradiated with illumination light SL to be described below.

In the present embodiment, each of the units in the processor 4 may be configured as individual electronic circuit, or may be configured as a circuit block in an integrated circuit such as an FPGA (field programmable gate array). In the present embodiment, for example, the processor 4 may include one or more CPUs. By an appropriate modification of the configuration according to the present embodiment, for example, a computer (not shown) may read a program for causing the functions of each unit of the processor 4 to be performed from a storage medium such as a memory, and perform an operation in response to the read program.

The display apparatus 5 includes an LCD (liquid crystal display), for example, and is configured to be able to display the observation image and the like to be outputted from the processor 4.

Then, the operation of the present embodiment will be described below.

A user such as a surgeon connects the units in the endoscope system 1 to turn on power, and then operates the observation mode changeover switch in the scope switch 23 to perform an instruction to set the observation mode of the endoscope system 1 to the white light observation mode.

The control unit 45 reads the control information WCJ from the memory 45a when detecting that the instruction to set the observation mode of the endoscope system 1 to the white light observation mode has been issued. Further, the control unit 45 generates a control signal for simultaneously emitting the V light, the B light, the G light, the A light, and the R light from the light source apparatus 3 in response to the control information WCJ and outputs the generated control signal to the light source control unit 34. The control unit 45 generates a control signal for setting the light emission amount ratio in the light emission amounts EV, EB, EG, EA, and ER to a predetermined light emission amount ratio RWT in response to the control information WCJ, and outputs the generated control signal to the light source control unit 34. Further, the control unit 45 generates a control signal for setting the gain value GV to 1 in response to the brightness control information WBCJ included in the control information WCJ, and outputs the generated control signal to the gain adjustment unit 42. The control unit 45 generates a control signal for causing an operation to be performed corresponding to the control information WCJ, and outputs the generated control signal to the image processing unit 43 and the observation image generation unit 44.

The light source control unit 34 generates, in response to the control signal outputted from the control unit 45, an LED drive signal for causing the violet LED 31a, the blue LED 31b, the green LED 31c, the amber LED 31d, and the red LED 31e to emit light at the same time and with a predetermined light emission amount ratio RWT in the white light observation mode, and outputs the generated LED drive signal to the light emitting unit 31. The illumination light WL including the V light, the B light, the G light, the A light, and the R light is emitted from the light source apparatus 3 (light emitting unit 31) in response to the operation of the light source control unit 34 in the white light observation mode, the object is irradiated with the illumination light WL, and image data WDI obtained by an image pickup of the return light (reflected light) of the illumination light WL is outputted to each of the brightness detection unit 41 and the gain adjustment unit 42 from the image pickup unit 21.

Figure 2:
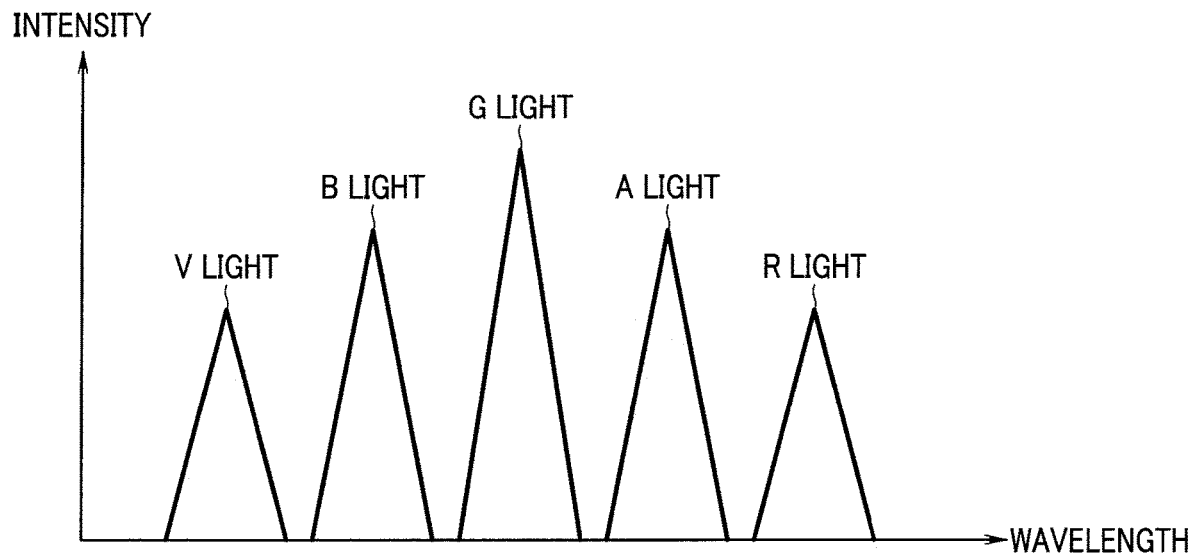
FIG. 2 is a view showing an example of a spectrum of illumination light with which an object is irradiated when an observation mode of the endoscope system according to the embodiment is set to a white light observation mode.

In the present embodiment, the predetermined light emission amount ratio RWT is set to satisfy a relation of EV=ER<EB=EA<EG, for example. For this reason, in the following description, for example, as shown in FIG. 2, the object is irradiated with the illumination light WL containing the largest amount of G light among five colors of light emitted from the light emitting unit 31 at the same time. In the present embodiment, when the observation mode of the endoscope system 1 is set to the white light observation mode, an image of the object illuminated by the illumination light WL having a spectrum as shown in FIG. 2 is picked up. Therefore, in the present embodiment, a pixel value is obtained for each pixel of the image data WDI, the pixel value having a luminance value of a blue component corresponding to the received light amount of the V light and the B light contained in the return light of the illumination light WL, a luminance value of a green component corresponding to the received light amount of the G light contained in the return light, and a luminance value of a red component corresponding to the received light amount of the A light and the R light contained in the return light. FIG. 2 is a view showing an example of a spectrum of illumination light, with which the object is irradiated, when the observation mode of the endoscope system according to the present embodiment is set to the white light observation mode.

The gain adjustment unit 42 sets the gain value GV to 1 in response to the control signal outputted from the control unit 45, and performs gain adjustment processing of multiplying the image data WDI outputted from the endoscope 2 by the set gain value GV. In addition, the gain adjustment unit 42 outputs the image data WDI subjected to the above-described gain adjustment processing to the image processing unit 43.

The image processing unit 43 performs, based on the control signal outputted from the control unit 45, color separation processing on the image data WDI outputted through the gain adjustment unit 42, for example, and thus generates an image data WVDI of a violet component corresponding to the V light contained in the return light of the illumination light WL with which the object is irradiated, an image data WBDI of a blue component corresponding to the B light contained in the return light, an image data WGDI of a green component corresponding to the G light contained in the return light, an image data WADI of an amber component corresponding to the A light contained in the return light, and an image data WRDI of a red component corresponding to the R light contained in the return light. Then, the image processing unit 43 outputs the image data of the respective color components obtained by the above-described color separation processing to the observation image generation unit 44.

The observation image generation unit 44 generates an observation image WLG in the white light observation mode based on the control signal outputted from the control unit 45 by, for example, assigning a luminance value obtained by addition of the image data WVDI and WBDI outputted through the image processing unit 43 to a B (blue) channel of the display apparatus 5, assigning a luminance value of the image data WGDI outputted through the image processing unit 43 to a G (green) channel of the display apparatus 5, and assigning a luminance value obtained by addition of the image data WADI and WRDI outputted through the image processing unit 43 to an R (red) channel of the display apparatus 5, and outputs the generated observation image WLG to the display apparatus 5.

The brightness detection unit 41 performs brightness detection processing for detecting the brightness of the image data WDI outputted from the endoscope 2, generates brightness detection information WBSJ indicating the brightness detected by the brightness detection processing, and outputs the generated information to the control unit 45.

More specifically, the brightness detection unit 41 calculates an average value of the luminance values of the respective pixels included in the image data WDI as a brightness detection value WDB, generates brightness detection information indicating the calculated brightness detection value WDB, and outputs the generated information to the control unit 45. When the object is irradiated with the illumination light as shown in FIG. 2, the brightness detection value WDB is equal to or substantially equal to the average value of the luminance values of the green components of the respective pixels included in the image data WDI.

The control unit 45 sets the brightness target value TWA in the white light observation mode when detecting that the instruction to set the observation mode of the endoscope system 1 to the white light observation mode has been issued. The control unit 45 performs, based on the brightness detection information WBSJ outputted from the brightness detection unit 41 and the brightness control information WBCJ included in the control information WCJ, an operation related to brightness control such that the brightness of the observation image displayed on the display apparatus 5 is closer to the brightness target value TWA.

Here, a specific example of the brightness control performed by the control unit 45 in the white light observation mode will be described. In the following description, a case will be described as a typical example in which the light emission amount EG of the green LED 31c among the five color LEDs serving as generation sources of the illumination light WL in the white light observation mode is changed. Further, according to the present embodiment, control is performed in the white light observation mode such that a predetermined light emission amount ratio RWT is maintained and the light emission amount of the four color LEDs other than the green LED 31c is changed by the same method as the specific example described below.

The control unit 45 specifies, based on the brightness control information WBCJ, a lower limit value WDBL of the brightness detection value WDB calculated by the brightness detection unit 41, an upper limit value WDBU of the brightness detection value WDB, and threshold values WDB1 and WDB2 (WDB1<WDB2) corresponding to the brightness detection values WDB. Further, the control unit 45 specifies the brightness detection value WDB based on the brightness detection information WBSJ outputted from the brightness detection unit 41.

For example, when detecting that the brightness detection value WDB belongs to a range of the lower limit value WDBL or more and less than the threshold value WDB1, based on the brightness target value TWA and the brightness control information WBCJ set within the range, the control unit 45 generates a control signal for causing a current value of the LED drive signal to be supplied to the green LED 31c to be set to a current value IM, and for causing a pulse width of the LED drive signal to be changed to any pulse width less than a pulse width PN by performing PWM (pulse width modulation) according to the brightness detection value WDB, and outputs the generated control signal to the light source control unit 34. Further, for example, when detecting that the brightness detection value WDB belongs to the range of the lower limit value WDBL or more and less than the threshold value WDB1, the control unit 45 generates a control signal for setting the gain value to 1, based on the brightness control information WBCJ, and outputs the generated control signal to the gain adjustment unit 42. The pulse width PN is preferably such a pulse width that a duty ratio is 1.

Figure 3:
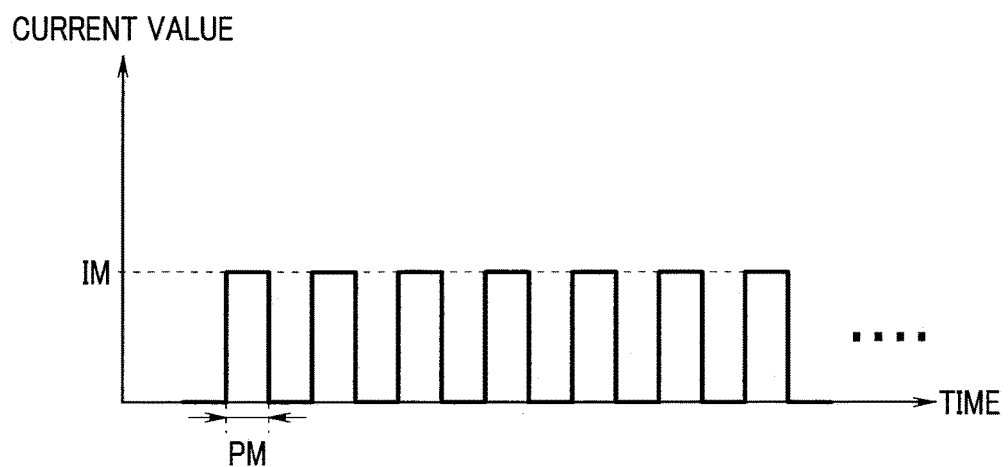
FIG. 3 is a view illustrating an example of a signal supplied to an LED provided in a light source apparatus according to the embodiment.

The light source control unit 34 supplies, in response to the control signal outputted from the control unit 45, a pulse signal having a current value IM and a pulse width PM less than the pulse width PN as shown in FIG. 3 to the green LED 31c, as an LED drive signal, when the brightness detection value WDB is the lower limit value WDBL, for example. FIG. 3 is a view illustrating an example of a signal to be supplied to the LED provided in the light source apparatus according to the embodiment.

In response to the control signal outputted from the control unit 45, the gain adjustment unit 42 sets the gain value GV to 1, and performs gain adjustment processing for multiplying the image data WDI outputted from the endoscope 2 by the set gain value GV.

For example, when detecting that the brightness detection value WDB belongs to a range of the threshold value WDB1 or more and less than the threshold value WDB2, based on the brightness target value TWA and the brightness control information WBCJ set within the range, the control unit 45 generates a control signal for causing a pulse width of the LED drive signal to be supplied to the green LED 31c to be set to the pulse width PN, and for causing the current value of the LED drive signal to be changed to any current value belonging to a range of the current value IM or more and less than the current value IN by performing PAM (pulse amplitude modulation) according to the brightness detection value WDB, and outputs the generated control signal to the light source control unit 34. Further, for example, when detecting that the brightness detection value WDB belongs to the range of the threshold value WDB1 or more and less than the threshold value WDB2, the control unit 45 generates a control signal for setting the gain value to 1, based on the brightness control information WBCJ, and outputs the generated control signal to the gain adjustment unit 42.

Figure 4:
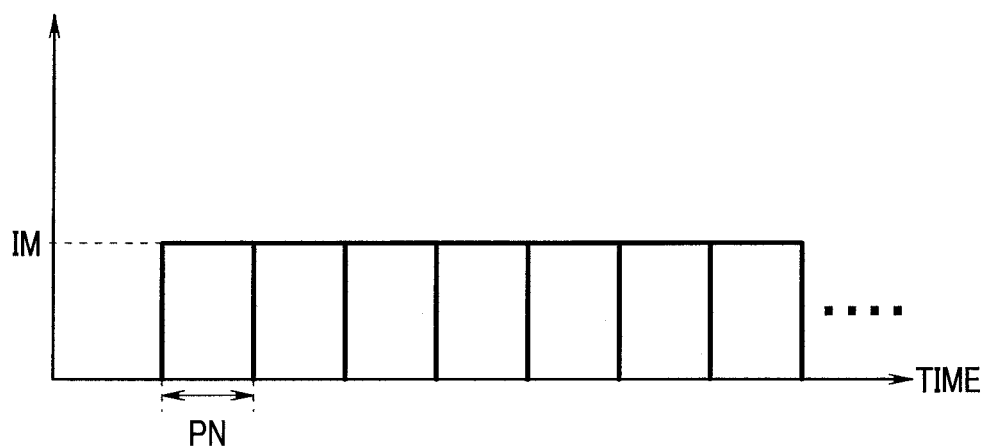
FIG. 4 is a view illustrating an example of a signal supplied to the LED provided in the light source apparatus according to the embodiment.

The light source control unit 34 supplies, in response to the control signal outputted from the control unit 45, a pulse signal having a current value IM and a pulse width PN larger than the pulse width PM as shown in FIG. 4 to the green LED 31c, as an LED drive signal, when the brightness detection value WDB is the threshold value WDB1, for example. FIG. 4 is a view illustrating an example of a signal to be supplied to the LED provided in the light source apparatus according to the embodiment.

In response to the control signal outputted from the control unit 45, the gain adjustment unit 42 sets the gain value GV to 1, and performs gain adjustment processing for multiplying the image data WDI outputted from the endoscope 2 by the set gain value GV.

For example, when detecting that the brightness detection value WDB belongs to a range of the threshold value WDB2 or more and the upper limit value WDBU or less, based on the brightness control information WBCJ, the control unit 45 generates a control signal for causing a pulse width of the LED drive signal to be supplied to the green LED 31c to be set to the pulse width PN and for causing the current value of the LED drive signal to be set to the current value IN, and outputs the generated control signal to the light source control unit 34. Further, for example, when detecting that the brightness detection value WDB belongs to the range of the threshold value WDB2 or more and the upper limit value WDBU or less, the control unit 45 generates, based on the brightness target value TWA and the brightness control information WBCJ set within the range, a control signal for changing the gain value to any gain value of 1 or more and GMAX or less according to the brightness detection value WDB, and outputs the generated control signal to the gain adjustment unit 42.

The gain value GMAX is a gain value corresponding to an upper limit value of the gain value GV used in the gain adjustment processing of the gain adjustment unit 42. The gain value GMAX may be a fixed value set in advance, or may be a variable value that can be changed by the user.

Figure 5:
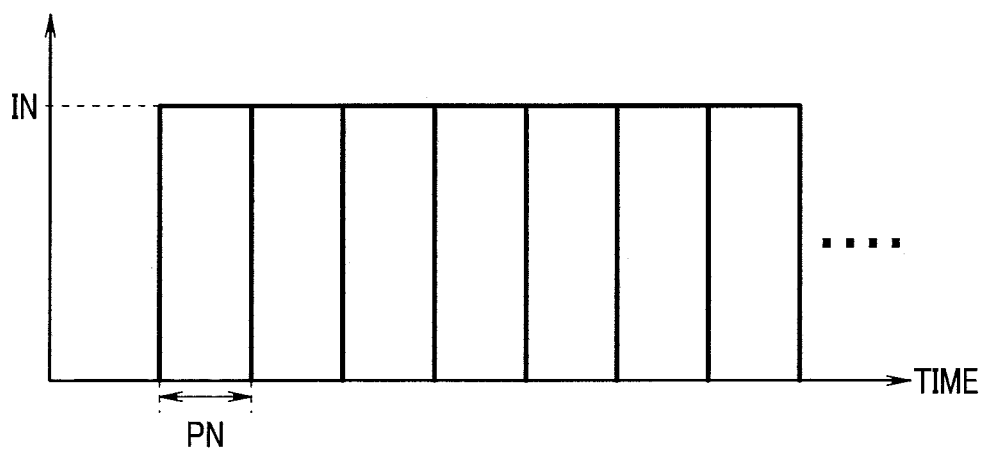
FIG. 5 is a view illustrating an example of a signal supplied to the LED provided in the light source apparatus according to the embodiment.

The light source control unit 34 supplies, in response to the control signal outputted from the control unit 45, a pulse signal having a current value IN and a pulse width PN as shown in FIG. 5 to the green LED 31c, as an LED drive signal, when the brightness detection value WDB belongs to a range of the threshold value WDB2 or more and the upper limit value WDBU or less, for example. FIG. 5 is a view illustrating an example of a signal to be supplied to the LED provided in the light source apparatus according to the embodiment.

In response to the control signal outputted from the control unit 45, the gain adjustment unit 42 sets the gain value GV to any value of 1 or more and GMAX or less, and performs gain adjustment processing for multiplying the image data WDI outputted from the endoscope 2 by the set gain value GV. In addition, the gain adjustment unit 42 outputs the image data WDI subjected to the above-described gain adjustment processing to the image processing unit 43.

In the brightness control as described above, the control unit 45 may preferably specify the threshold value WDB1 as an upper limit value when the brightness of the image data WDI acquired in the white light observation mode is changed by the PWM. In the brightness control as described above, the control unit 45 may preferably specify the threshold value WDB2 as an upper limit value when the brightness of the image data WDI acquired in the white light observation mode is changed by the PAM.

Figure 6:
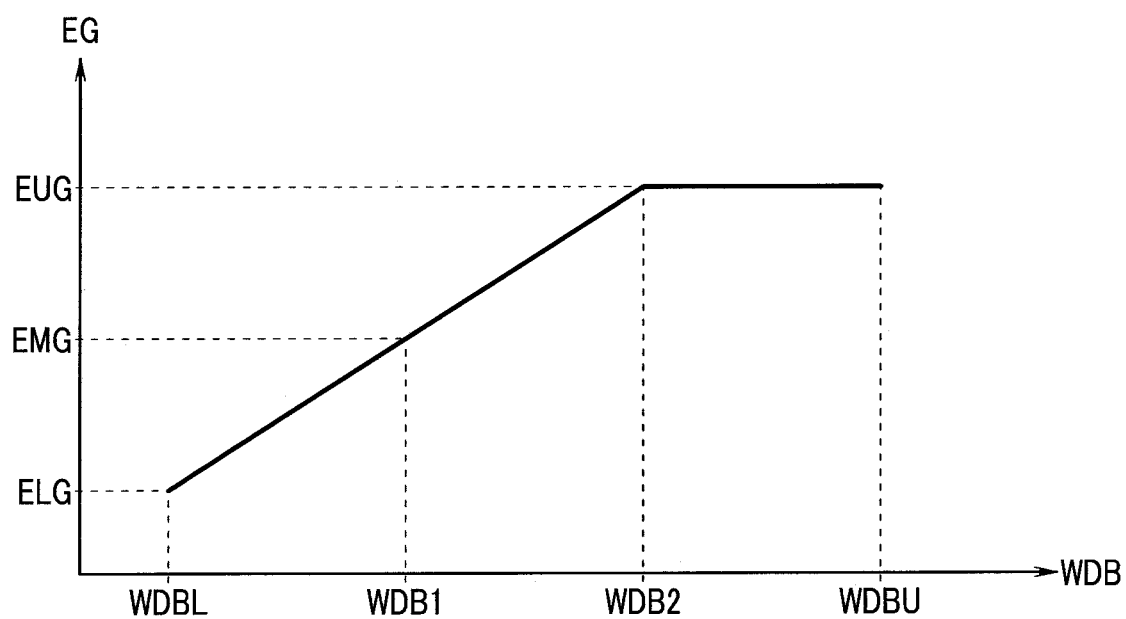
FIG. 6 is a view illustrating an example of a relation between a brightness detection value and a light emission amount of the LED when the observation mode of the endoscope system according to the embodiment is set to a white light observation mode.

According to the brightness control as described above, in the white light observation mode, the light emission amount EG of the green LED 31c changes according to the brightness detection value WDB as illustrated in FIG. 6. FIG. 6 is a view illustrating an example of a relation between the brightness detection value and the light emission amount of the LED when the observation mode of the endoscope system according to the embodiment is set to the white light observation mode.

More specifically, when the brightness detection value WDB belongs to the range of the lower limit value WDBL or more and less than the threshold value WDB1, the light emission amount EG changes within a range of a minimum light emission amount ELG or more and less than the light emission amount EMG (>ELG) depending on an application period of the current applied to the green LED 31c. Further, when the brightness detection value WDB belongs to the range of the threshold value WDB1 or more and less than the threshold value WDB2, the light emission amount EG changes within a range of the light emission amount EMG or more and less than a maximum light emission amount EUG (>EMG) depending on a current value of the current applied to the green LED 31c. When the brightness detection value WDB belongs to the range of the threshold value WDB2 or more and the upper limit value WDBU or less, the light emission amount EG is maintained at the maximum light emission amount EUG.

For this reason, according to the brightness control as described above, for example, when the brightness detection value WDB belongs to the range of the lower limit value WDBL or more and less than the threshold value WDB1, the gain value GV is fixed to 1, the light emission amount of each of the LEDs of the light emitting unit 31 is changed, and thus the brightness of the observation image WLG displayed on the display apparatus 5 can be set to a brightness suitable for near view observation. According to the brightness control as described above, for example, when the brightness detection value WDB belongs to the range of the threshold value WDB1 or more and less than the threshold value WDB2, the gain value GV is fixed to 1, the light emission amount of each of the LEDs of the light emitting unit 31 is changed, and thus the brightness of the observation image WLG displayed on the display apparatus 5 can be set to a brightness suitable for mid-range view observation. According to the brightness control as described above, for example, when the brightness detection value WDB belongs to the range of the threshold value WDB2 or more and upper limit value WDBU or less, the light emission amount of each of the LEDs of the light emitting unit 31 is fixed, the gain value GV is changed, and thus the brightness of the observation image WLG displayed on the display apparatus 5 can be set to a brightness suitable for distant view observation.

The user inserts the insertion portion 2a of the endoscope 2 into the inside of an examinee and arranges the distal end portion 2c near a desired object existing inside the examinee while confirming the observation image WLG displayed on the display apparatus 5. Thereafter, the user operates the observation mode changeover switch of the scope switch 23 in the state where the distal end portion 2c of the endoscope 2 is arranged near the desired object to perform an instruction to set the observation mode of the endoscope system 1 to the special light observation mode.

The control unit 45 reads the control information SCJ from the memory 45a when detecting that the instruction to set the observation mode of the endoscope system 1 to the special light observation mode has been issued. Further, the control unit 45 generates a control signal for simultaneously emitting the G light, the A light, and the R light from the light source apparatus 3 in response to the control information SCJ and outputs the generated control signal to the light source control unit 34. The control unit 45 generates a control signal for setting the light emission amount ratio in the light emission amounts EG, EA, and ER to a predetermined light emission amount ratio RST in response to the control information SCJ, and outputs the generated control signal to the light source control unit 34. Further, the control unit 45 generates a control signal for setting the gain value GV to 1 in response to the brightness control information SBCJ included in the control information SCJ, and outputs the generated control signal to the gain adjustment unit 42. The control unit 45 generates a control signal for causing an operation to be performed corresponding to the control information SCJ, and outputs the generated control signal to the image processing unit 43 and the observation image generation unit 44.

The light source control unit 34 generates, in response to the control signal outputted from the control unit 45, an LED drive signal for causing the violet LED 31a and the blue LED 31b to quench light and for causing the green LED 31c, the amber LED 31d, and the red LED 31e to emit light at the same time and with a predetermined light emission amount ratio RST in the special light observation mode, and outputs the generated LED drive signal to the light emitting unit 31. The illumination light SL including the G light, the A light, and the R light is emitted from the light source apparatus 3 (light emitting unit 31) in response to the operation of the light source control unit 34 in the special light observation mode, the object is irradiated with the illumination light SL, and image data SDI obtained by an image pickup of the return light (reflected light) of the illumination light SL is outputted to each of the brightness detection unit 41 and the gain adjustment unit 42 from the image pickup unit 21.

Figure 7:
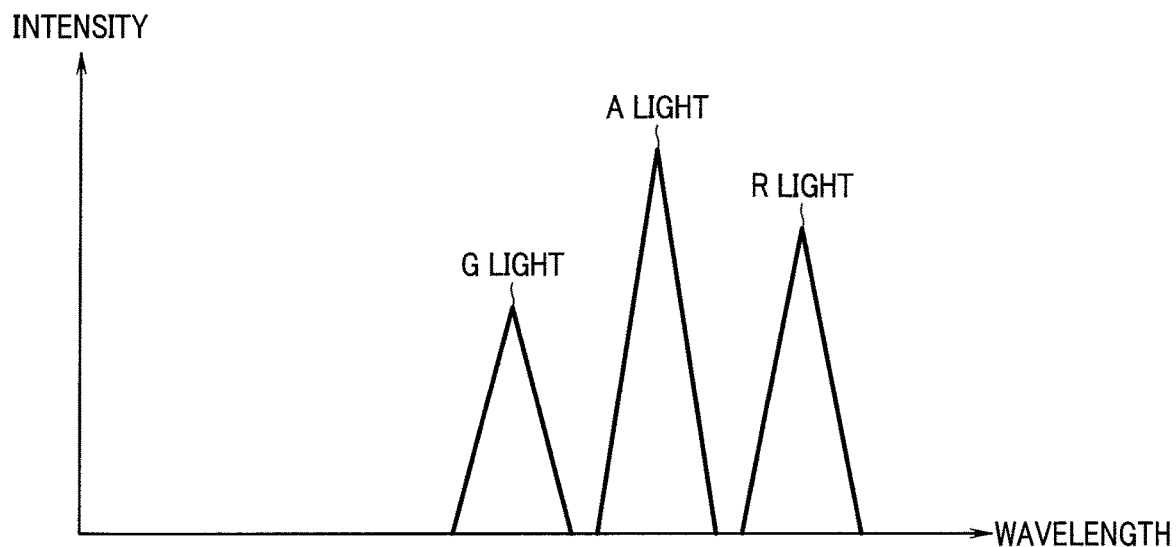
FIG. 7 is a view showing an example of a spectrum of illumination light with which an object is irradiated when the observation mode of the endoscope system according to the embodiment is set to a special light observation mode.

In the present embodiment, the predetermined light emission amount ratio RST is set to satisfy a relation of EG<ER<EA, for example. For this reason, in the following description, for example, as shown in FIG. 7, the object is irradiated with the illumination light SL containing the largest amount of A light among three colors of light emitted from the light emitting unit 31 at the same time. In the present embodiment, when the observation mode of the endoscope system 1 is set to the special light observation mode, an image of the object illuminated by the illumination light SL having a spectrum as shown in FIG. 7 is picked up. Therefore, in the present embodiment, a pixel value is obtained for each pixel of the image data SDI, the pixel value having a luminance value of a green component corresponding to the received light amount of the G light contained in the return light of the illumination light SL, and a luminance value of a red component corresponding to the received light amount of the A light and the R light contained in the return light. FIG. 7 is a view showing an example of a spectrum of illumination light, with which the object is irradiated, when the observation mode of the endoscope system according to the present embodiment is set to the special light observation mode.

The gain adjustment unit 42 sets the gain value GV to 1 in response to the control signal outputted from the control unit 45, and performs gain adjustment processing of multiplying the image data SDI outputted from the endoscope 2 by the set gain value GV. In addition, the gain adjustment unit 42 outputs the image data SDI subjected to the above-described gain adjustment processing to the image processing unit 43.

The image processing unit 43 performs, based on the control signal outputted from the control unit 45, color separation processing on the image data SDI outputted through the gain adjustment unit 42, for example, and thus generates an image data SGDI of a green component corresponding to the G light contained in the return light of the illumination light SL with which the object is irradiated, an image data SADI of an amber component corresponding to the A light contained in the return light, and an image data SRDI of a red component corresponding to the R light contained in the return light. Then, the image processing unit 43 outputs the image data of the respective color components obtained by the above-described color separation processing to the observation image generation unit 44.

The observation image generation unit 44 generates an observation image SLG in the special light observation mode based on the control signal outputted from the control unit 45 by, for example, assigning a luminance value of the image data SGDI outputted through the image processing unit 43 to a B (blue) channel of the display apparatus 5, assigning a luminance value of the image data SADI outputted through the image processing unit 43 to a G (green) channel of the display apparatus 5, and assigning a luminance value of the image data SRDI outputted through the image processing unit 43 to an R (red) channel of the display apparatus 5, and outputs the generated observation image SLG to the display apparatus 5.

The brightness detection unit 41 performs brightness detection processing for detecting the brightness of the image data SDI outputted from the endoscope 2, generates brightness detection information SBSJ indicating the brightness detected by the brightness detection processing, and outputs the generated information to the control unit 45.

More specifically, the brightness detection unit 41 calculates an average value of the luminance values of the respective pixels included in the image data SDI as a brightness detection value SDB, generates brightness detection information indicating the calculated brightness detection value SDB, and outputs the generated information to the control unit 45. When the object is irradiated with the illumination light as shown in FIG. 7, the brightness detection value SDB is equal to or substantially equal to the average value of the luminance values of the red components of the respective pixels included in the image data SDI.

The control unit 45 sets the brightness target value TSA in the special light observation mode when detecting that the instruction to set the observation mode of the endoscope system 1 to the special light observation mode has been issued. The control unit 45 performs, based on the brightness detection information SBSJ outputted from the brightness detection unit 41 and the brightness control information SBCJ included in the control information SCJ, an operation related to brightness control such that the brightness of the observation image displayed on the display apparatus 5 is closer to the brightness target value TSA.

Here, a specific example of the brightness control performed by the control unit 45 in the special light observation mode will be described. In the following description, when the observation mode of the endoscope system 1 is set to the special light observation mode, a case will be described in which a wavelength shift occurs according to the magnitude of the currents of the LED drive signals supplied to the three color LEDs serving as generation sources of the illumination light SL. In the following description, a case will be described as a typical example in which the light emission amount EA of the amber LED 31d among the three color LEDs serving as generation sources of the illumination light SL in the special light observation mode is changed. Further, according to the present embodiment, control is performed in the special light observation mode such that a predetermined light emission amount ratio RST is maintained and the light emission amount of the two color LEDs other than the amber LED 31d is changed by the same method as the specific example described below.

The control unit 45 specifies, based on the brightness control information SBCJ, a lower limit value SDBL of the brightness detection value SDB calculated by the brightness detection unit 41, an upper limit value SDBU of the brightness detection value SDB, and threshold values SDB1 and SDB2 (SDB1<SDB2) corresponding to the brightness detection values SDB. Further, the control unit 45 specifies the brightness detection value SDB based on the brightness detection information SBSJ outputted from the brightness detection unit 41.

For example, when detecting that the brightness detection value SDB belongs to a range of the lower limit value SDBL or more and less than the threshold value SDB1, based on the brightness target value TSA and the brightness control information SBCJ set within the range, the control unit 45 generates a control signal for causing a current value of the LED drive signal to be supplied to the amber LED 31d to be set to a current value IS, and for causing a pulse width of the LED drive signal to be changed to any pulse width less than a pulse width PT by performing PWM (pulse width modulation) according to the brightness detection value SDB, and outputs the generated control signal to the light source control unit 34. Further, for example, when detecting that the brightness detection value SDB belongs to the range of the lower limit value SDBL or more and less than the threshold value SDB1, the control unit 45 generates a control signal for setting the gain value to 1, based on the brightness control information SBCJ, and outputs the generated control signal to the gain adjustment unit 42. The pulse width PT is preferably such a pulse width that a duty ratio is 1.

In other words, when detecting that the brightness detection value SDB belongs to the brightness range of the lower limit value SDBL or more and less than the threshold value SDB1, the control unit 45 performs control to change the application period of the current supplied to each of the LEDs serving as the generation sources of the illumination light SL.

Figure 8:
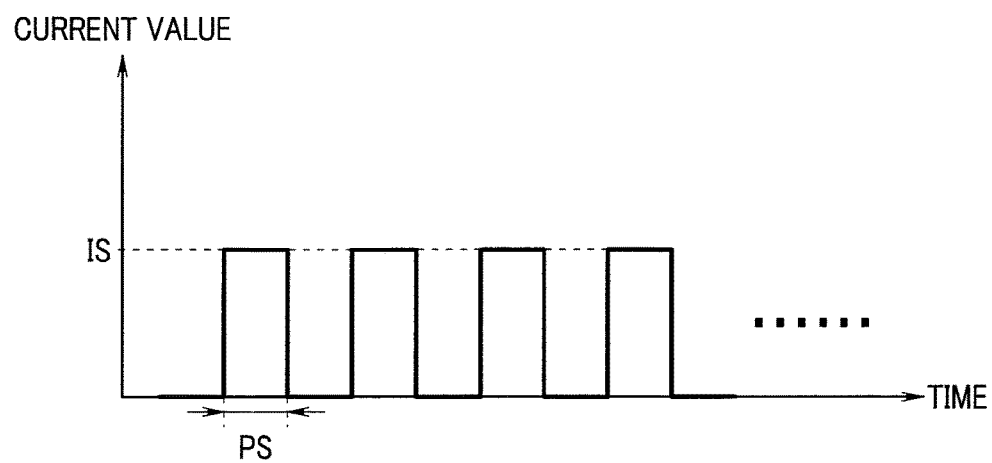
FIG. 8 is a view illustrating an example of a signal supplied to the LED provided in the light source apparatus according to the embodiment.

The light source control unit 34 supplies, in response to the control signal outputted from the control unit 45, a pulse signal having a current value IS and a pulse width PS less than the pulse width PT as shown in FIG. 8 to the amber LED 31d, as an LED drive signal, when the brightness detection value SDB is the lower limit value SDBL, for example. FIG. 8 is a view illustrating an example of a signal to be supplied to the LED provided in the light source apparatus according to the embodiment.

In response to the control signal outputted from the control unit 45, the gain adjustment unit 42 sets the gain value GV to 1, and performs gain adjustment processing for multiplying the image data SDI outputted from the endoscope 2 by the set gain value GV.

For example, when detecting that the brightness detection value SDB belongs to a range of the threshold value SDB1 or more and less than the threshold value SDB2, based on the brightness control information SBCJ, the control unit 45 generates a control signal for causing a pulse width of the LED drive signal to be supplied to the amber LED 31d to be set to the pulse width PT, and for causing the current value of the LED drive signal to be set to a current value IS, and outputs the generated control signal to the light source control unit 34. Further, for example, when detecting that the brightness detection value SDB belongs to the range of the threshold value SDB1 or more and less than the threshold value SDB2, the control unit 45 generates a control signal for causing the gain value to be changed to any gain value of 1 or more and less than GMAX according to the brightness detection value SDB, based on the brightness target value TSA and the brightness control information SBCJ set within the range, and outputs the generated control signal to the gain adjustment unit 42.

In other words, when detecting that the brightness detection value SDB belongs to the brightness range of the threshold value SDB1 or more and less than the threshold value SDB2, the control unit 45 performs control to maintain the current value of the current supplied to each of the LEDs serving as the generation sources of the illumination light SL as the current value IS, to maintain the application period of the current supplied to each of the LEDs as the pulse width PT, and to change the gain value by which the image data SDI is multiplied.

Figure 9:
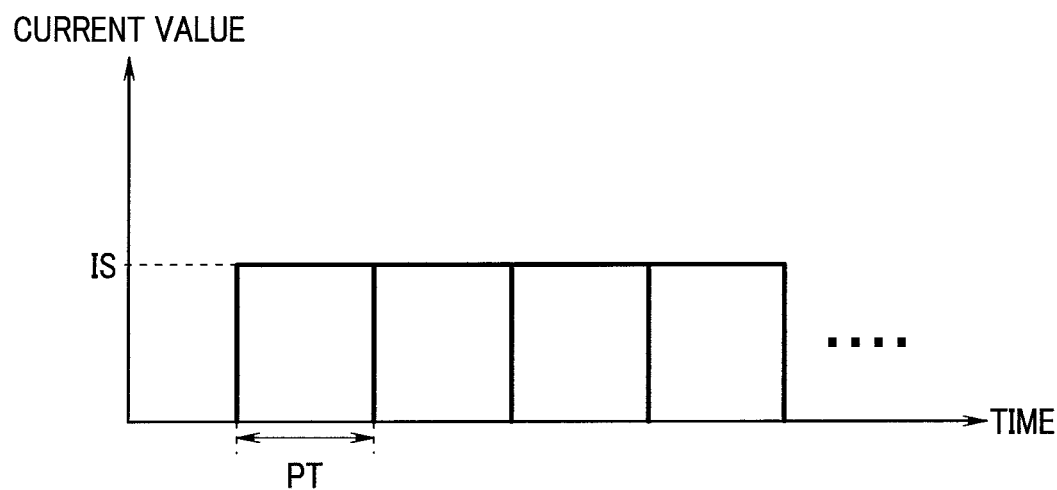
FIG. 9 is a view illustrating an example of a signal supplied to the LED provided in the light source apparatus according to the embodiment.

The light source control unit 34 supplies, in response to the control signal outputted from the control unit 45, a pulse signal having a current value IS and a pulse width PT larger than the pulse width PS as shown in FIG. 9 to each of the LEDs of the light emitting unit 31, as an LED drive signal, when the brightness detection value SDB belongs to the range of the threshold value SDB1 or more and less than the threshold value SDB2, for example. FIG. 9 is a view illustrating an example of a signal to be supplied to the LED provided in the light source apparatus according to the embodiment.

In response to the control signal outputted from the control unit 45, the gain adjustment unit 42 sets the gain value GV to any gain value of 1 or more and less than GMAX, and performs gain adjustment processing for multiplying the image data SDI outputted from the endoscope 2 by the set gain value GV. Further, the gain adjustment unit 42 outputs the image data SDI subjected to the above-described gain adjustment processing to the image processing unit 43.

For example, when detecting that the brightness detection value SDB belongs to a range of the threshold value SDB2 or more and the upper limit value SDB or less, based on the brightness target value TSA and the brightness control information SBCJ set within the range, the control unit 45 generates a control signal for causing a pulse width of the LED drive signal to be supplied to the amber LED 31*d* to be set to the pulse width PT, and for causing the current value of the LED drive signal to be changed to any current value belonging to a range of larger than the current value IS and the current value IT or less by performing PAM (pulse amplitude modulation) according to the brightness detection value SDB, and outputs the generated control signal to the light source control unit 34. Further, for example, when detecting that the brightness detection value SDB belongs to the range of the threshold value SDB2 or more and the upper limit value SDB or less, the control unit 45 generates a control signal for setting the gain value to GMAX, based on the brightness control information SBCJ, and outputs the generated control signal to the gain adjustment unit 42.

In other words, when detecting that the brightness detection value SDB belongs to the brightness range of the threshold value SDB2 or more and the upper limit value SDBU or less, the control unit 45 performs control to maintain the gain value, by which the image data SDI is multiplied, at GMAX and to change the current value of the current applied to each of the LEDs serving as the generation sources of the illumination light SL.

Figure 10:
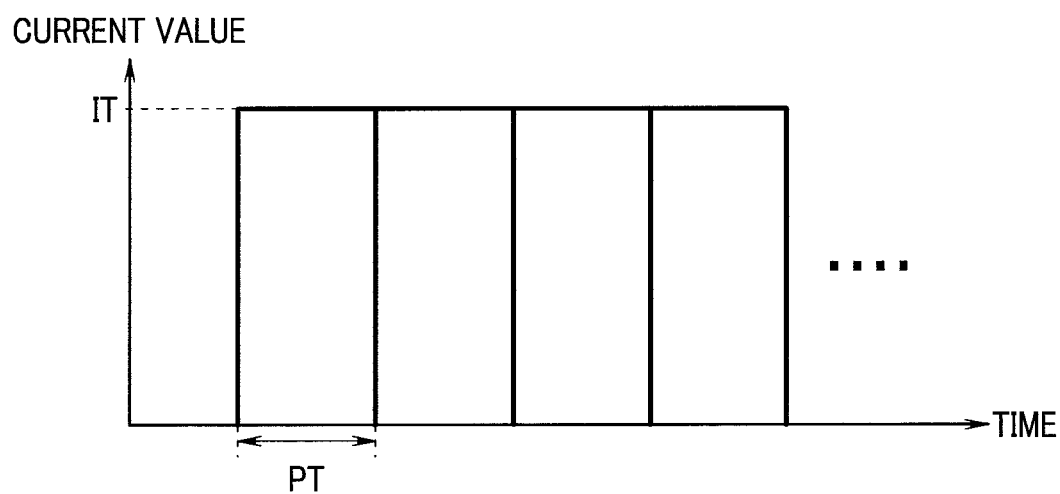
FIG. 10 is a view illustrating an example of a signal supplied to the LED provided in the light source apparatus according to the embodiment.

The light source control unit 34 supplies, in response to the control signal outputted from the control unit 45, a pulse signal having a current value IT and a pulse width PT as shown in FIG. 10 to each of the LEDs of the light emitting unit 31, as an LED drive signal, when the brightness detection value SDB is the upper limit value SDBU, for example. FIG. 10 is a view illustrating an example of a signal to be supplied to the LED provided in the light source apparatus according to the embodiment.

In response to the control signal outputted from the control unit 45, the gain adjustment unit 42 sets the gain value GV to GMAX, and performs gain adjustment processing for multiplying the image data SDI outputted from the endoscope 2 by the set gain value GV.

In the brightness control as described above, the control unit 45 may preferably specify the threshold value SDB1 as an upper limit value when the brightness of the image data SDI acquired in the special light observation mode is changed by the PWM. In the brightness control as described above, the control unit 45 may preferably specify the threshold value SDB2 as an upper limit value when the brightness of the image data SDI acquired in the special light observation mode is changed by the gain adjustment processing of the gain adjustment unit 42.

Figure 11:
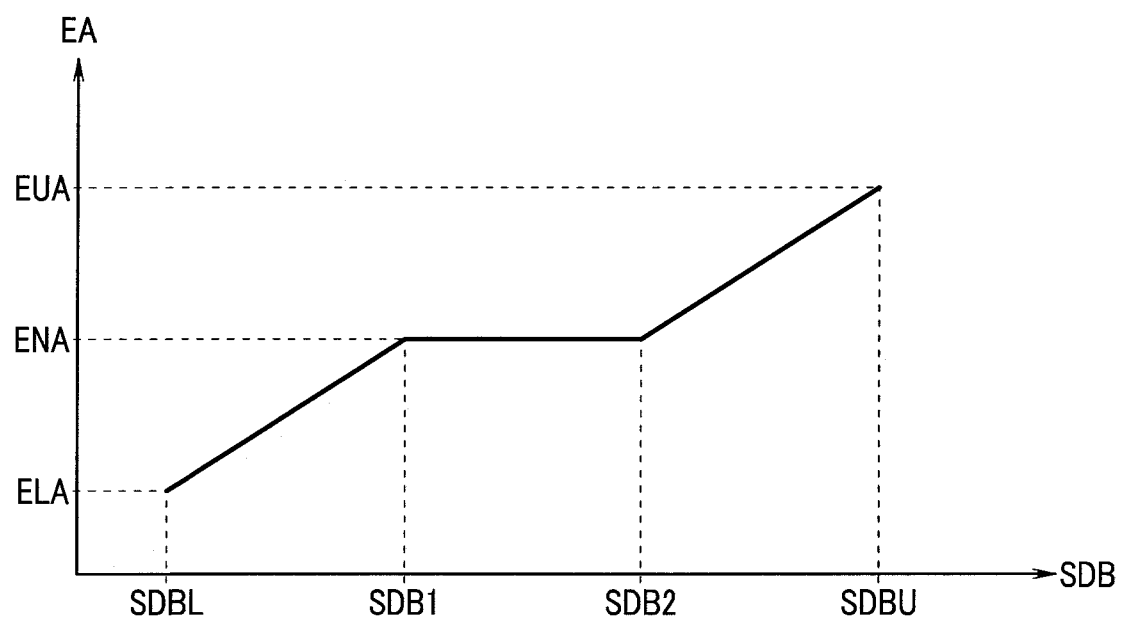
FIG. 11 is a view illustrating an example of a relation between a brightness detection value and a light emission amount of the LED when the observation mode of the endoscope system according to the embodiment is set to a special light observation mode.

According to the brightness control as described above, in the special light observation mode, the light emission amount EA of the amber LED 31*d* changes according to the brightness detection value SDB as illustrated in FIG. 11. FIG. 11 is a view illustrating an example of a relation between the brightness detection value and the light emission amount of the LED when the observation mode of the endoscope system according to the embodiment is set to the special light observation mode.

More specifically, when the brightness detection value SDB belongs to the range of the lower limit value SDBL or more and less than the threshold value SDB1, the light emission amount EA changes within a range of a minimum light emission amount ELA or more and less than the light emission amount EMA (>ELA) depending on an application period of the current applied to the amber LED 31*d*. When the brightness detection value SDB belongs to the range of the threshold value SDB1 or more and less than the threshold value SDB2, the light emission amount EA is maintained at the light emission amount EMA. Further, when the brightness detection value SDB belongs to the range of the threshold value SDB2 or more and upper limit value SDBU or less, the light emission amount EA changes within a range of more than the light emission amount EMA and a maximum light emission amount EUA (>EMA) or less depending on a current value of the current applied to the amber LED 31*d*.

For this reason, according to the brightness control as described above, for example, when the brightness detection value SDB belongs to the range of the lower limit value SDBL or more and less than the threshold value SDB1, the gain value GV is fixed to 1, the light emission amount of the green LED 31*c*, the amber LED 31*d*, and the red LED 31*e* is changed, and thus the brightness of the observation image SLG displayed on the display apparatus 5 can be set to a brightness suitable for near view observation. According to the brightness control as described above, for example, when the brightness detection value SDB belongs to the range of the threshold value SDB1 or more and less than the threshold value SDB2, the light emission amount of the green LED 31*c*, the amber LED 31*d*, and the red LED 31*e* is fixed, the gain value GV is changed, and thus the brightness of the observation image SLG displayed on the display apparatus 5 can be set to a brightness suitable for mid-range view observation. According to the brightness control as described above, for example, when the brightness detection value SDB belongs to the range of the threshold value SDB2 or more and upper limit value SDBU or less, the gain value GV is fixed to GMAX, the light emission amount of the green LED 31*c*, the amber LED 31*d*, and the red LED 31*e* is changed, and thus the brightness of the observation image SLG displayed on the display apparatus 5 can be set to a brightness suitable for distant view observation.

Generally, in the endoscope observation in the medical field, the work related to the search for a lesion site is performed in a distant view, and the work related to the diagnosis of the lesion site is performed in a mid-range view and a near view. Therefore, the brightness of the observation image displayed on the display apparatus tends to be more important than the color tone of the observation image during the distant view observation. In the mid-range view and the near view observation, the brightness of the observation image displayed on the display apparatus and the color tone of the observation image tend to be almost equally important. In the special light observation mainly used for the work related to the diagnosis of the lesion site, it is necessary to improve the visibility of the lesion site as compared with the white light observation. For this reason, the color tone of the observation image displayed on the display apparatus tends to be more important in the special light observation than in the white light observation.

Further, when the semiconductor light source such as the LED is used as a light source for endoscope observation, a situation may occur in which an observation image having a color tone different from the original color tone is displayed due to an occurrence of a wavelength shift that is a phenomenon in which a peak wavelength of the light emitted from the semiconductor light source is shifted from the original peak wavelength according to the magnitude of the current applied to the semiconductor light source.

On the other hand, according to the present embodiment, since the brightness control is performed in the special light observation mode to prevent the change in color tone due to the occurrence of the wavelength shift and to improve the brightness of the observation image, the observation image having a color tone capable of ensuring accuracy related to the diagnosis of the lesion site can be displayed on the display apparatus 5 during the mid-range observation and the near view observation, for example. Therefore, according to the present embodiment, when the semiconductor light source is used for the light source for endoscope observation, the display of the observation image having a color tone different from the original color tone can be prevented as much as possible.

According to the present embodiment, for example, in the brightness control of the white light observation mode and the brightness control of the special light observation mode, the control for causing PWM to be performed and the control for causing PAM to be performed may be mutually exchanged. In such a case, the threshold value WDB1 is specified as an upper limit value when the brightness of the image data WDI acquired in the white light observation mode is changed by the PAM. In the above-described case, the threshold value WDB2 is specified as an upper limit value when the brightness of the image data WDI acquired in the white light observation mode is changed by the PWM.

In other words, according to the present embodiment, the control unit 45 may perform an operation according to a control pattern CPA in which, in the brightness control in the special light observation mode, control CA is performed to change one of the current value and the application period of the current applied to each of the LEDs serving as the generation sources of the illumination light SL when the brightness detection value SDB belongs to a brightness range RSA of the lower limit value SDBL or more and less than the threshold value SDB1, control CB is performed to change the gain value GV when the brightness detection value SDB belongs to a brightness range RSB of the threshold value SDB1 or more and less than the threshold value SDB2, and control CC is performed to change the other of the current value and the application period of the current applied to each of the LEDs when the brightness detection value SDB belongs to a brightness range RSC of the threshold value SDB2 or more and the upper limit value SDBU or less. In addition, according to the present embodiment, the control unit 45 may perform an operation according to a control pattern CPB in which, in the brightness control in the white light observation mode, control CD is performed to change one of the current value and the application period of the current applied to each of the LEDs serving as the generation sources of the illumination light WL when the brightness detection value WDB belongs to a brightness range RSD of the lower limit value WDBL or more and less than the threshold value WDB1, control CE is performed to change the other of the current value and the application period of the current applied to each of the LEDs when the brightness detection value WDB belongs to a brightness range RSE of the threshold value WDB1 or more and less than the threshold value WDB2, and control CF is performed to change the gain value GV when the brightness detection value WDB belongs to a brightness range RSF of the threshold value WDB2 or more and the upper limit value WDBU or less.

According to the present embodiment, for example, in the special light observation mode, as long as the control for changing the gain value GV is performed between the control for causing the PWM to be performed and the control for causing the PAW to be performed, brightness control different from the above-described brightness control may be performed.

According to the present embodiment, for example, when the image pickup device 21*b* includes an electronic shutter, control for changing a shutter speed in the electronic shutter may be performed instead of the control for changing the gain value GV.

According to the present embodiment, for example, when the image pickup device 21*b* has a binning function, control for changing the number of pixels to be handled as one pixel group in the binning function may be performed instead of the control for changing the gain value GV.

According to the present embodiment, for example, the memory 45*a* may store brightness control information corresponding to each of three or more observation modes including a white light observation mode and a special light observation mode.

According to the present embodiment, for example, instead of the green LED 31*c*, a phosphor light source may be provided in the light emitting unit 31, the phosphor light source including a semiconductor light source that generates blue excitation light and a phosphor that is excited by the blue excitation light and generates green fluorescence. In other words, according to the present embodiment, for example, a light source, which is more difficult to shift the wavelength than the green LED 31*c*, may be provided in the light emitting unit 31.

Further, by appropriate modification of the configuration according to the present embodiment, the present invention may be adapted to the image pickup device in which a color filter such as a complementary color filter other than the primary color Bayer arrangement is provided on the image pickup surface.

Further, by appropriate modification of the configuration according to the present embodiment, the present invention may be adapted to the image pickup device such as a monochrome image sensor in which a color filter is not provided on the image pickup surface.

The present invention is not limited to the embodiment described above, and it goes without saying that various modifications and applications can be made within the scope without departing from the gist of the present invention.

What is claimed is:

1. An endoscope system comprising:
    a light source comprising a plurality of semiconductor light sources, and configured to generate illumination light including first light having a peak wavelength in a first wavelength and second light having a peak wavelength in a second wavelength, the second wavelength being on a short wavelength side compared with the first wavelength;
    an image sensor configured to pick up an image of an object irradiated with the illumination light to obtain the image; and
    a processor comprising hardware, the processor being configured to:
        control the light source to switch between a first illumination mode in which the object is irradiated with, as the illumination light, first illumination light containing the first light more than the second light and a second illumination mode in which the object is irradiated with, as the illumination light, second illumination light containing the second light more than the first light; and
        select, according to a brightness of the image, one of control for changing an application period of a current applied to the plurality of semiconductor light sources, control for changing a current value of the current applied to the plurality of semiconductor light sources, or control for changing a gain value to be multiplied to the image;
    wherein the processor is configured to perform an operation according to a first control pattern, when the first illumination mode is selected as an illumination mode,
    in the first control pattern, the processor performs:
        a first control to change the application period of the current applied to the plurality of semiconductor light sources, when the brightness of the image belongs to a first brightness range;
        a second control to change the brightness of the image by predetermined processing, to which the image is subjected, when the brightness of the image belongs to a second brightness range brighter than the first brightness range; and
        a third control to change the current value of the current applied to the plurality of semiconductor light sources, when the brightness of the image belongs to a third brightness range brighter than the second brightness range.

2. The endoscope system according to claim 1, wherein the processor is configured to:
    perform, as the first control, control for changing the application period of the current applied to the plurality of semiconductor light sources, which is the generation source of the illumination light, to any application period less than a predetermined application period;
    perform, as the second control, control for maintaining the application period of the current applied to the plurality of semiconductor light sources, which is the generation source of the illumination light, at the predetermined application period and changing the gain value to be multiplied in gain adjustment processing, to which the image is subjected, to any gain value less than a predetermined gain value; and
    perform, as the third control, control for maintaining the application period of the current applied to the plurality of semiconductor light sources, which is the generation source of the illumination light, at the predetermined application period, maintaining the gain value to be multiplied in the gain adjustment processing at the predetermined gain value, and changing the current value of the current applied to the plurality of semiconductor light sources which is the generation source of the illumination light.

3. The endoscope system according to claim 1, wherein the processor is configured to specify a first threshold value corresponding to an upper limit value of the first brightness range as an upper limit value when the brightness of the image is changed by the first control, and to specify a second threshold value corresponding to an upper limit value of the second brightness range as an upper limit value when the brightness of the image is changed by the second control.

4. The endoscope system according to claim 1, wherein the peak wavelength of the first light is set to any wavelength between 585 nm and 615 nm.

5. The endoscope system according to claim 1, wherein
    the processor is configured to perform an operation according to a second control pattern, when the second illumination mode is selected as the illumination mode,
    in the second control pattern, the processor performs:
        a fourth control to change the application period of the current applied to the plurality of semiconductor light sources, when the brightness of the image belongs to a fourth brightness range;
        a fifth control to change the current value of the current applied to the plurality of semiconductor light sources, when the brightness of the image belongs to a fifth brightness range brighter than the fourth brightness range; and
        a sixth control to change the brightness of the image by predetermined processing, to which the image is subjected, when the brightness of the image belongs to a sixth brightness range brighter than the fifth brightness range.

6. A processor for an endoscope for use with a light source apparatus and the endoscope, the light source apparatus comprising a plurality of semiconductor light sources and being configured to generate illumination light including first light having a peak wavelength in a first wavelength and second light having a peak wavelength in a second wavelength, the second wavelength being on a short wavelength side compared with the first wavelength,
    the endoscope being configured to pick up an image of an object irradiated with the illumination light to obtain the image,
    the processor for the endoscope being configured to:
        control the plurality of semiconductor light sources to switch between a first illumination mode in which the object is irradiated with, as the illumination light, first illumination light containing the first light more than the second light and a second illumination mode in which the object is irradiated with, as the illumination light, second illumination light containing the second light more than the first light; and
        select, according to a brightness of the image, one of control for changing an application period of a current applied to the plurality of semiconductor light sources, control for changing a current value of the current applied to the plurality of semiconductor light sources, or control for changing a gain value to be multiplied to the image;

wherein the processor for the endoscope is configured to perform an operation according to a first control pattern, when the first illumination mode is selected as an illumination mode, in the first control pattern, the processor for the endoscope performs:
- a first control to change the application period of the current applied to the plurality of semiconductor light sources, when the brightness of the image belongs to a first brightness range;
- a second control to change the brightness of the image by predetermined processing, to which the image is subjected, when the brightness of the image belongs to a second brightness range brighter than the first brightness range; and
- a third control to change the current value of the current applied to the plurality of semiconductor light sources, when the brightness of the image belongs to a third brightness range brighter than the second brightness range.

7. A method of controlling an endoscope system including a light source apparatus and an endoscope, the light source apparatus comprising a plurality of semiconductor light sources and being configured to generate illumination light including first light having a peak wavelength in a first wavelength and second light having a peak wavelength in a second wavelength, the second wavelength being on a short wavelength side compared with the first wavelength, the endoscope being configured to pick up an image of an object irradiated with the illumination light to obtain the image, the method comprising:
controlling the plurality of semiconductor light sources to switch between a first illumination mode in which the object is irradiated with, as the illumination light, first illumination light containing the first light more than the second light and a second illumination mode in which the object is irradiated with, as the illumination light, second illumination light containing the second light more than the first light; and
selecting, according to a brightness of the image, one of control for changing an application period of a current applied to the plurality of semiconductor light sources, control for changing a current value of the current applied to the plurality of semiconductor light sources, or control for changing a gain value to be multiplied to the image;
wherein the controlling of the plurality of semiconductor light sources performs an operation according to a first control pattern, when the first illumination mode is selected as an illumination mode,
in the first control pattern, the controlling performs:
- a first control to change the application period of the current applied to the plurality of semiconductor light sources, when the brightness of the image belongs to a first brightness range;
- a second control to change the brightness of the image by predetermined processing, to which the image is subjected, when the brightness of the image belongs to a second brightness range brighter than the first brightness range; and
- a third control to change the current value of the current applied to the plurality of semiconductor light sources, when the brightness of the image belongs to a third brightness range brighter than the second brightness range.

8. A non-transitory computer-readable recording medium that stores an image processing program which a computer is caused to execute, the computer-readable recording medium causing an endoscope system to execute a control process and a selection process, the endoscope system including a light source apparatus and an endoscope, the light source apparatus comprising a plurality of semiconductor light sources and being configured to generate illumination light including first light having a peak wavelength in a first wavelength and second light having a peak wavelength in a second wavelength, the second wavelength being on a short wavelength side compared with the first wavelength, the endoscope being configured to pick up an image of an object irradiated with the illumination light to obtain the image,
the control process controlling the plurality of semiconductor light sources to switch between a first illumination mode in which the object is irradiated with, as the illumination light, first illumination light containing the first light more than the second light and a second illumination mode in which the object is irradiated with, as the illumination light, second illumination light containing the second light more than the first light; and
the selection process selecting, according to a brightness of the image, one of control for changing an application period of a current applied to the plurality of semiconductor light sources, control for changing a current value of the current applied to the plurality of semiconductor light sources, or control for changing a gain value to be multiplied to the image;
wherein the control process performs an operation according to a first control pattern, when the first illumination mode is selected as an illumination mode,
in the first control pattern, the control process performs:
- a first control to change the application period of the current applied to the plurality of semiconductor light sources, when the brightness of the image belongs to a first brightness range;
- a second control to change the brightness of the image by predetermined processing, to which the image is subjected, when the brightness of the image belongs to a second brightness range brighter than the first brightness range; and
- a third control to change the current value of the current applied to the plurality of semiconductor light sources, when the brightness of the image belongs to a third brightness range brighter than the second brightness range.

* * * * *